United States Patent [19]

Fenton

[11] Patent Number: 4,654,037
[45] Date of Patent: Mar. 31, 1987

[54] OSTOMY POUCH IRRIGATOR

[75] Inventor: Leonard Fenton, Beachwood, Ohio

[73] Assignee: Marlen Manufacturing and Development Co., Bedford, Ohio

[21] Appl. No.: 819,715

[22] Filed: Jan. 17, 1986

[51] Int. Cl.⁴ .............................................. A61F 5/44
[52] U.S. Cl. .................................... 604/334; 604/277
[58] Field of Search ....................... 604/277, 332–335

[56] References Cited

U.S. PATENT DOCUMENTS

| | | | |
|---|---|---|---|
| 2,928,393 | 3/1960 | Maisan | 604/344 |
| 2,973,759 | 3/1961 | Plymale, Jr. | 604/344 |
| 3,910,274 | 10/1975 | Nolan | 604/277 |
| 4,134,404 | 1/1979 | Williams, Jr. | 604/277 |

Primary Examiner—J. L. Kruter
Attorney, Agent, or Firm—Pearne, Gordon, McCoy & Granger

[57] ABSTRACT

An ostomy pouch having a self-contained irrigator for cleaning the pouch. The pouch comprises spaced front and back walls sealed about their peripheries to define a collecting chamber and has a closable bottom opening for draining the collected contents of the pouch for disposal. An opening is provided in one of the walls for receiving the stoma of a patient. A fluid distribution tube is located within the pouch and is provided with a multiplicity of openings so that a projecting end of the tube may be connected to a source of cleansing fluid to permit the contents of the pouch to be flushed from the pouch without removing the pouch from the patient's body.

6 Claims, 4 Drawing Figures

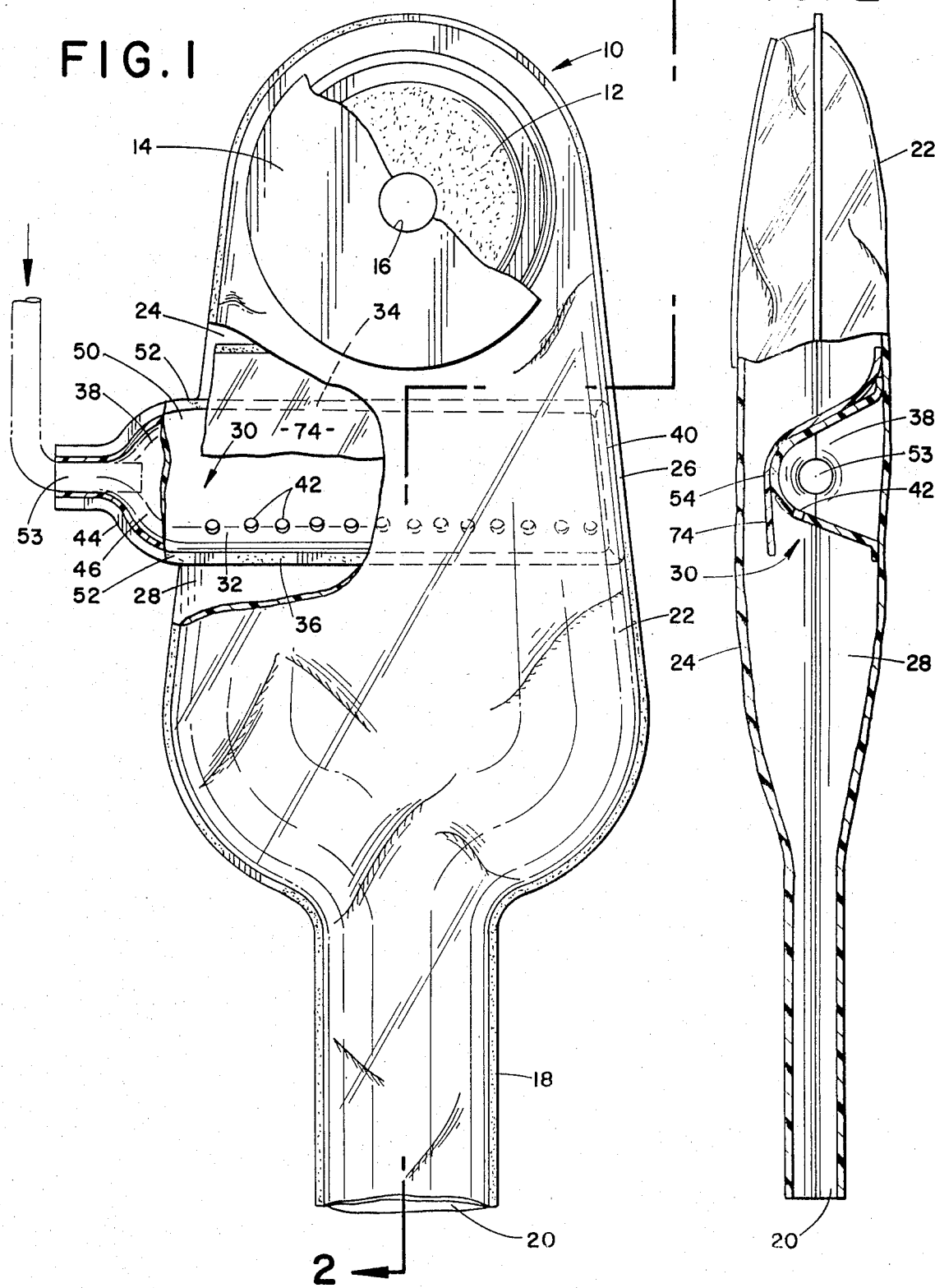

OSTOMY POUCH IRRIGATOR

BACKGROUND OF THE INVENTION

This invention relates to ostomy devices and, more particularly, to an ostomy pouch having a selfcontained irrigator for cleansing the pouch after use.

Ostomy surgical procedures, such as colostomies, ileostomies, and urostomies, create an exit for feces from the colon in formed, semiformed, or semiliquid effluents or an exit for urine which is diverted before it reaches the bladder. Drainage from the stoma is collected in a bag or pouch which is attached to the body by a suitable adhesive and/or a mounting belt worn by the patient. The stoma protrudes into an opening in the bag and intermittently discharges waste with little or no control by the individual. The bag or pouch may be disposable with its contents, but a more accepted arrangement is a reusable bag having a discharge opening so that the bag may be flushed with an irrigating liquid such as water to cleanse the interior of the bag at suitable intervals.

The conventional way to empty and flush ostomy pouches is to remove the pouch from its applied position relative to the stoma, release the fastening device from the drainage neck of the pouch, and flush the contents and clean the bag by inserting the tip of an irrigating tube through the stoma opening provided in the side wall of the bag. This operation is not only messy, but does not always result in the thorough cleaning of the interior of the bag below the stoma opening. Moreover, since conventional pouches must be removed from the body for cleaning, the skin surrounding the stoma opening may become irritated by frequent removal and reapplication of an adhesively mounted pouch.

SUMMARY OF THE INVENTION

This invention provides an arrangement for flushing and irrigating an ostomy pouch by a simple technique employing an irrigator arrangement built into the ostomy pouch. According to this invention, there is provided a flexible tube within the interior of the pouch sealed to one of the pouch walls and having an inlet tip projecting from the ostomy pouch for connection to an irrigation tube. During use, the projecting tip is adapted to be sealed to prevent the escape of odors from the pouch. This arrangement permits the contents of the pouch to be flushed from the pouch without removing the pouch from the body.

According to one aspect of the present invention, the tube is formed by a strip of plastic having its edges sealed to one of the walls forming the ostomy pouch and the inlet tip is formed by a projection of the wall to which the strip is sealed and the strip itself. The other wall, of course, is sealed to the strip at the juncture of the strip and the periphery of the pouch to provide a completely sealed ostomy pouch. A multiplicity of downwardly directed openings are provided in the tube to direct streams of an irrigating fluid, such as water, downwardly against the interior of the pouch so that waste matter may be completely flushed from the pouch through a resealable opening formed at the bottom of the pouch.

According to another aspect of this invention, the tube comprises a flexible conduit sealed to one of the walls which define the pouch and which projects through and is sealed to a seam of the pouch to provide an inlet spout for the admission of irrigating fluid to the tube. A multiplicity of downwardly directed openings are provided in the tube so that the previously described pouch irrigating operation may be performed.

BRIEF DESCRIPTION OF THE DRAWING

FIG. 1 is an elevational view of an ostomy pouch according to one aspect of this invention, with portions broken away for clarity;

FIG. 2 is a cross-sectional view, the plane of the section being indicated by the line 2—2 in FIG. 1;

DETAILED DESCRIPTION OF THE INVENTION

Figure 3:
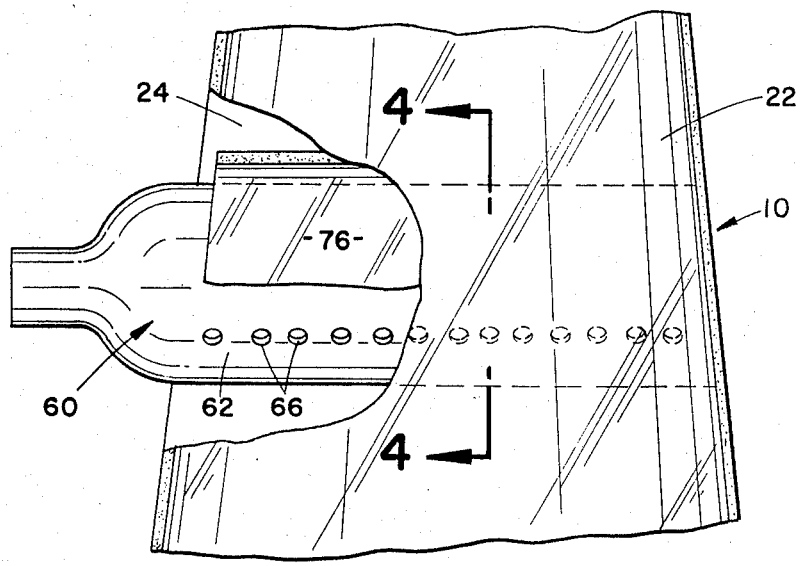
FIG. 3 is a fragmentary, elevational view similar to FIG. 1, but showing an ostomy pouch according to another aspect of this invention, with portions broken away for clarity.

Referring now to the drawings, and particularly to FIGS. 1 and 2, there is illustrated an ostomy pouch 10 having a self-contained irrigator for cleaning the pouch without removing the pouch from the body. The pouch 10 is made of a suitable elastomeric material and may be secured to the patient by a suitable belt (not shown) or may be secured to the patient by an adhesive 12 covered by protective release paper 14. The pouch 10 has an inlet opening 16 formed in the upper portion of the pouch which is adapted to receive the stoma of the patient. A lower end portion 18 of the pouch includes an outlet opening 20 through which waste is removed. The opening 20 is closed when in use by folding the lower end portion 18 of the pouch back on itself and securing the fold by any suitable clasp. A particularly desirable clasp for securing the lower end 18 of the pouch is disclosed in U.S. Pat. No. 4,460,359.

The pouch 10 is formed by a front section or wall 22 and a rear section or wall 24. The marginal edges of the walls 22 and 24 are sealed along a perimeter 26 to define the pouch cavity or receptacle 28.

To permit the cavity 28 to be thoroughly flushed and cleansed between uses on the patient, or even while the pouch 10 is mounted on the patient, an irrigating tube 30 is provided. According to the aspect of the invention illustrated in FIGS. 1 and 2, the irrigating tube 30 comprises an elongated strip 32 of elastomeric material which is sealed along its longitudinal edges 34 and 36 to the wall 22 to form a fluid distribution passage 38. The distal end of the passage 38 is sealed at 40 between the seal formed by the peripheral seal 26 joining the walls 22 and 24. A multiplicity of openings 42 are formed along the length above the strip 32 and are preferably positioned to be directed downwardly toward the opening 20 for effective removal of the contents of the pouch 10. The proximal end 44 of the tube 30 projects from one edge of the pouch 10 and is formed by a lip portion 46 of the wall 24 and by a projecting end 50 of the strip 32. The lip portion 46 and the end 50 are sealed at their parallel edges 52, but are open at their ends to provide an inlet opening 53 for connection to an irrigation tube connected to a source of irrigating fluid such as water. The intersection of the portion 50 and the strip 32 is sealed to the wall 22 at a seam 54 to ensure that the cavity 28 will be leakproof.

Figure 4:
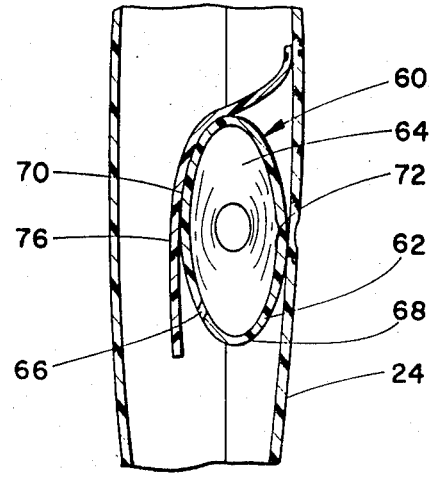
FIG. 4 is a cross-sectional view, the plane of the section being indicated by the line 4—4 of FIG. 3.

Referring now to FIGS. 3 and 4, there is illustrated an irrigation tube 60 according to another aspect of this invention. The tube 60 comprises a length of cylindrical tubing 62 sealed at its distal end between the front and rear walls 22 and 24 of the pouch 10 and defining a fluid distribution chamber 64. The tubing is provided with a multiplicity of openings 66 to direct cleansing fluid downwardly toward the opening 20 in the pouch. The proximal end of the tubing 62 projects from the side of the pouch 10 between the walls 22 and 24, and is sealed to the walls 22 and 24 at seams 68 and 70. The projecting end of the tubing 62 is connected to an irrigation tube which is in communication with a source of fluid cleanser, such as water. As may be seen in FIG. 4, the tubing 62 is sealed to the wall 24 along a seam 72.

In order to prevent waste material from fouling the openings 66 and 42 in the tubes 30 and 60, flaps 74 and 76 forming a deflector strip may be attached to the wall 24 to extend over the tubes 30 and 60. The flaps 74 and 76 also aid in directing the cleaning fluid downwardly toward the opening 20 in the pouch 10.

Although the preferred embodiment of this invention has been shown and described, it should be understood that various modifications and rearrangements of the parts may be resorted to without departing from the scope of the invention as disclosed and claimed herein.

What is claimed is:

1. An ostomy pouch having a self-contained irrigator for cleaning the pouch, said pouch comprising a pair of spaced, flexible, plastic walls sealed about their peripheries to define a collecting chamber and having a closable bottom opening for draining the collected contents of said pouch for disposal, an opening in one of said walls for receiving the stoma of a patient, means defining a flexible plastic tube along the other of said walls, means defining an inlet to said tube from the outside of said pouch, said inlet being adapted to be connected to a source of cleaning fluid, said tube being fixed to and extending along the wall opposite said opening within said pouch and extending beyond an edge of said pouch and being sealed to the peripheries of said walls, and a plurality of passageways from said tube to said collecting chamber, whereby the collecting chamber can be emptied and flushed by opening said bottom opening and connecting said inlet to a source of cleaning fluid.

2. An ostomy pouch according to claim 1, wherein a deflector strip is attached to said other of said walls and overlies said passageways.

3. An ostomy pouch according to claim 1, wherein said plastic tube is defined in part by a portion of one of said walls and in part by a strip of plastic sealed to said one of said walls along parallel, spaced, peripheral edges of said strip, said strip being provided with said passageways.

4. An ostomy pouch according to claim 3, wherein said plastic tube has an inlet spout projecting from said pouch and being adapted to be closed during use of the pouch on the patient.

5. An ostomy pouch having a self-contained irrigator for cleaning the pouch, said pouch comprising a pair of spaced, flexible, plastic walls sealed about their peripheries to define a collecting chamber and having a closable bottom opening for draining the collected contents of said pouch for disposal, an opening in one of said walls for receiving the stoma of the patient, means defining a fluid passageway along the other of said walls, means defining an inlet to said passageway from the outside of said pouch, said inlet being adapted to be connected to a source of cleaning fluid, a plurality of passageways within said pouch from said fluid passageway to said collecting chamber, and a deflector strip attached to said other of said walls and overlying said passageways, whereby the collecting chamber can be emptied and flushed by opening said bottom opening and connecting said inlet to a source of cleaning fluid.

6. An ostomy pouch having a self-contained irrigator for cleaning the pouch, said pouch comprising a pair of spaced, flexible, plastic walls sealed about their peripheries to define a collecting chamber and having a closable bottom opening for draining the collected contents of said pouch for disposal, an opening in one of said walls for receiving the stoma of a patient, means defining a cylindrical, flexible, plastic tube along the other of said walls, means defining an inlet to said tube from the outside of said pouch, said inlet being adapted to be connected to a source of cleaning fluid, said tube being fixed to and extending along the wall opposite said opening and extending beyond the edge of said pouch and being sealed to the peripheries of said walls, and a plurality of passageways within said pouch fluidly communicating said tube to said collecting chamber, whereby the collecting chamber can be emptied and flushed by opening said bottom opening and connecting said inlet to a source of cleaning fluid.

* * * * *